United States Patent [19]

Brooks

[11] 4,181,589

[45] Jan. 1, 1980

[54] METHOD FOR SEPARATING BIOLOGICAL CELLS

[76] Inventor: Robert A. Frosch, Administrator of the National Aeronautics and Space Administration with respect to an invention of Donald E. Brooks, Vancouver, Canada

[21] Appl. No.: 17,888

[22] Filed: Mar. 6, 1979

[51] Int. Cl.[2] .......................................... G01N 27/26
[52] U.S. Cl. ........................... 204/180 R; 204/299 R; 424/12
[58] Field of Search .......... 204/180 R, 180 G, 180 S, 204/180 P, 299, 301; 424/12; 23/230 B

[56] References Cited

U.S. PATENT DOCUMENTS

| | | | |
|---|---|---|---|
| 3,305,471 | 2/1967 | Von Munchhausen et al. | 204/180 R X |
| 3,649,499 | 3/1972 | Virtanen et al. | 204/180 R |
| 3,847,773 | 11/1974 | Snyder | 204/180 R |
| 4,061,560 | 12/1977 | Hannig et al. | 204/299 R |
| 4,155,831 | 5/1979 | Bhattacharya | 204/299 R |

*Primary Examiner*—Arthur C. Prescott
*Attorney, Agent, or Firm*—Joseph H. Beumer; John R. Manning; L. D. Wofford, Jr.

[57] ABSTRACT

A method for separating biological cells characterized by the steps of suspending a mixed cell population in a body of aqueous polymer comprising a system consisting of phases for which said cells exhibit an affinity including at least one phase having droplets characterized by a first surface potential and at least one phase having droplets characterized by another surface potential, and subjecting said system to an electrostatic field established between a pair of electrodes, said field being of sufficient intensity for causing at least some of the droplets to migrate toward one of said electrodes with an attendant separation of the cells of said population.

8 Claims, 3 Drawing Figures

METHOD FOR SEPARATING BIOLOGICAL CELLS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The invention generally relates to a technique for achieving biological cell separation and more particularly to a method wherein the cells of a mixed cell population suspended in an aqueous polymer system are separated as a consequence of an electrophoretic separation of the phases of the system.

2. Description of the Prior Art

Much of the modern biomedical research is directly aimed at defining and classifying the normal and pathological activity of living systems. A principle problem in such work is frequently encountered when attempts are made to prepare a specific cell population of interest in a pure state. Nonspecific preparation techniques based on cell size or density are seldom sufficiently sensitive as the total range of these parameters encountered among biological organisms is relatively narrow.

Separation methods based on cell surface properties hold promise, however, since a cell's function and its ability to inter-react with cells in its immediate environment appear frequently to be reflected in characteristics of the cell's membrane. One such characteristic which is being exploited for preparative purposes is cell surface charge detected by electrophoresis. Free-flow electrophoresis is capable of spatially distributing a cell population on the basis of the net charge density located within ten to thirty angstroms of the hydrodynamic cell surface. An even more sensitive preparation technique is available, however, which depends partly on surface charge but which has been shown to be capable of separating cell populations which are electrophoretically indistinguishable.

When aqueous solutions of different polymers are mixed above certain concentrations they frequently form immisible-liquid two-phase solutions. Each of the phases usually consists of more than 90% water and can be buffered and made isotonic by the addition of molecular weight species. If a cell or particle suspension is added to such a system, then shaken, the cells, upon re-equilibration, are frequently found to have partitioned unequally between one phase and the interface. This preferential partition behavior can be used as a basis for separation procedures for differing cell populations since partition in these systems is determined directly by cell membrane properties.

Cell populations which have related, but not identical surface properties, seldom exhibit sufficiently different partition behavior to be separated in a single extraction. In such cases, multiple partitions are carried out via countercurrent distribution to effect the separation. Countercurrent distribution in phase systems derived from dextran/polyethylene glycol mixtures has proven to be an extremely sensitive and valuable preparation technique in cell biology. Erythrocyte populations can be separated on the basis of cell age by countercurrent distribution techniques. This separation can not be accomplished by preparatory electrophoresis. Countercurrent distribution of human lymphocytes fractionates them into subpopulations which vary markedly in their T:B ratio and in their responses to various mitogens. Again, preparatory electrophoresis has not yet proven capable of producing such a separation. The effectiveness of countercurrent distribution as a separation procedure residues in the fact that the partition coefficient, k, is sensitive to a variety of cell surface properties. Moreover, partition coefficient k depends exponentially on the effective cell surface charge of a cell in contrast to a linear dependency of electrophoretic mobility on cell charge. This relationship accounts, in part, for the relatively high sensity of countercurrent distribution over preparative electrophoresis.

The interfacial free energy of the cell/solution interface is a parameter which also contributes in determining partition coefficient k. This free energy will be determined largely by the degree to which one or the other of the phase polymers adsorbs to the cell surface, thus lowering the free energy between the polymer-coated cell and the phase in which the polymer predominates. The competitive adsorption of the two polymer phase depends, in turn, on the chemical nature of the polymers and on a variety of cell membrane properties. Few of these membrane properties have been identified as yet. However, it has been found that the chemical composition and structure of the cell membrane, independent of surface charge, also serves to determine partition behavior.

Countercurrent distribution techniques have been applied with success to relatively small biological cells such as erthrocytes and lymphocytes. There are a variety of cell types such as macrophages, megakaryocytes, and some tumor cells which are too large and/or too dense to be separated successfully in the phase systems currently employed. Such cells do not remain in suspension long enough to allow the phases to separate and permit a transfer along the countercurrent train.

By performing countercurrent distribution in a zero-gravity environment, or the low gravity environment of space, the problem can be eliminated. However, in a low-G environment the phases themselves do not separate effectively because of a lack of density difference.

It is, therefore, the general purpose of the instant invention to provide an improved method for separating biological cells employing two phase equeous polymer systems.

OBJECTS AND SUMMARY OF THE INVENTION

It is an object of the instant invention to provide an improved method for separating biological cells.

It is another object to provide an improved method for separating biological cells utilizing a two-phase aqueous polymer system in the absence of cell sedimentation.

It is another object to provide a method through which biological cell separation can be achieved in a gravitational field of one G without attendant cell sedimentation.

It is another object to provide a method for separating biological cells in a gravitational field of less than one G utilizing the two-phase aqueous polymer system, the phases being separated through an application of an electrical static field.

These and other objects and advantages are achieved through a method wherein countercurrent distribution is successfully applied to cells employing an electric field applied across an aqueous polymer system for effectively separating phase droplets in accordance with the surface charges thereof and an attendant separation of differing cell populations exhibiting an affinity for the different phases of the system, as will become more readily apparent in view of the description and claims in light of the accompanying drawings.

DESCRIPTION OF THE PREFERRED EMBODIMENT

Figure 1:
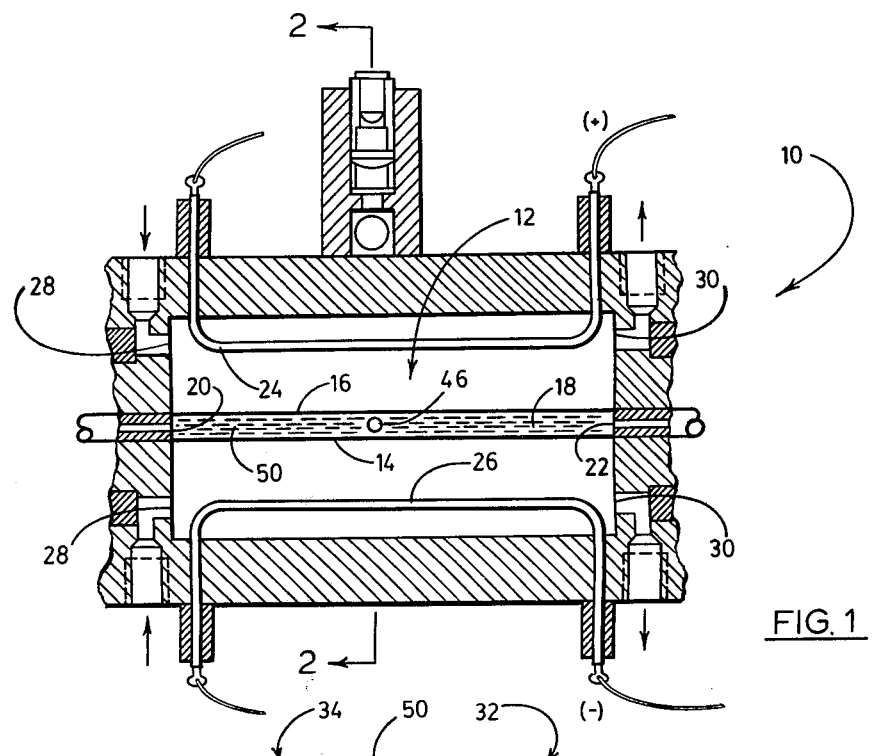
FIG. 1 is a fragmented, cross-sectional view of an apparatus employed in the performance of a method embodying the principles of the instant invention.
Figure 2:
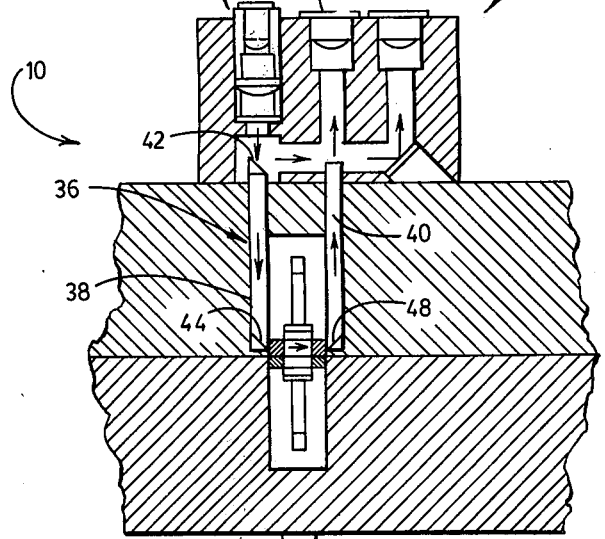
FIG. 2 is a cross-sectional view taken generally along line 2—2 on FIG. 1.
Figure 3:
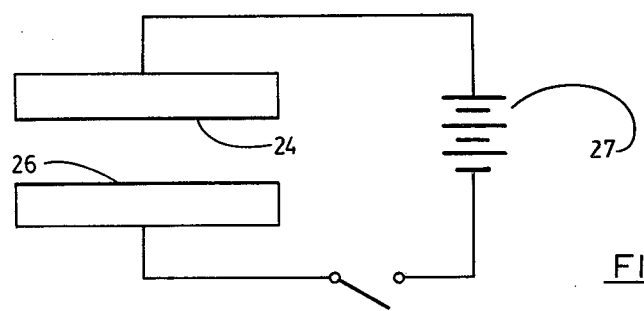
FIG. 3 is a schematic view illustrating a circuit employed for purposes of applying an electrostatic field across a two-phase aqueous polymer system.

Referring now to the drawings with more particularity, wherein like reference characters designate like or corresponding parts throughout the several views, there is shown in FIG. 1 a device 10 particularly suited for use in performing the method of the instant invention.

It is important to understand that the details of the device hereinafter described form no part of the claimed invention. Therefore, the device as described is deemed to typify a device adapted to perform the method embodying the principles of the instant invention and may be varied as required without departing from the scope of the invention.

The device 10, as shown, is particularly adapted for use in celestial space, or a low-gravity environment. As shown, the device 10 includes a cavity 12 of suitable dimensions having disposed therein a pair of mutually spaced membranes 14 and 16 defining therebetween a phase separation chamber, designated 18. While the material from which the membranes 14 and 16 are fabricated may be varied, as desired, Amicon XM-100 serves quite satisfactorily for this purpose.

Disposed in communication with the phase separation chamber 18 is an inlet 20 and an exit port 22. The purposes of the ports 20 and 22 are to accommodate an introduction into the separation chamber 18 of a two-phase aqueous polymer system, hereinafter to be more specifically described. Of course, the ports 20 and 22 may be open for accommodating a continous passage of a polymer system therethrough or, where so desired, may be closed for entrapping the system within the chamber 18. Moreover, while not shown, it is to be understood that the cavity 12 may be separated for facilitating access to the phase separation chamber 18 in order to facilitate extraction of separated cells.

Also projected into the cavity 12 is a first electrode 24 and a second electrode 26 connected to a suitable source of electrical potential 27 whereby electrostatic field selectively may be established therebetween. Due to the relative disposition of the electrodes 24 and 26 the established field extends across the chamber 18. As a practical matter, the electrodes 24 and 24 comprise bright platinum electrodes.

The cavity 12 also includes a pair of inlet ports 28 and a pair of exit ports 30 through which a rinse buffer is circulated to remove electrode reaction products, as well as to cool the electrodes, whereby the electrodes are protected.

Finally, the device 10 is provided with an optic system 32 which is used to follow phase separation turbidimetrically. The system 10 includes a small ruby laser 34 which provides a beam conducted through a light conduit 36 of a folded configuration having one segment 38 located at one side of the cavity 12 and another segment 40 located at the cavity's opposite side. Segment 38 of the conduit 36 includes a beam splitter surface 42 through which the beam passes to a reflective surface 44 positioned to direct the beam through a port 46 provided to establish a path for the beam through the cavity 12, between the membranes 14 and 16.

The segment 40 of the conduit 36, on the other hand, includes a surface 48 for collecting the laser beam and directing the beam along the segment 40 to a detector 50. Thus the beam intensity may be measured for determining the presence of a turbid mixed phase system which exists only in the presence of non-scattered light.

Again, it is important to appreciate that the details of the device 10 form no specific part of the claimed invention. Therefore, where so desired, the optic system 32 is varied or even omitted.

As shown, there is deposited within chamber 18 a body 50 of aqueous polymer comprising a system consisting of phases for which certain cells of a given population exhibit an affinity and is characterized by an electrophoretic mobility. Where desired, the body 50 comprises a flowing body, however, as shown, the body 50 comprises an entrapped body of a cell suspension medium having multiple phases which may be separated in the absence of gravity driven sedimentation.

It has been found that aqueous polymer systems consisting of Sodium Dextran Sulfate and Pluronic P-104 may be suspended in a supporting electrolyte comprising potassium citrate. One two-phase system utilized satisfactorily consists of 8% solution of Sodium Dextran Sulfate, 8% solution of P-104 and 0.2 molar potassium citrate. Another system employed satisfactorily consists of 5% solution of Sodium Dextran Sulfate, 10% solution of P-104 and 0.1 milliliters of potassium citrate.

Typical droplets mobilities, in units of $cm^2 v^{-1} s^{-1}$, for these systems are shown in the following table for 6.5 micron diameter drops: t,0060

In these systems the top phase is rich in P-104 and the bottom is predominately sodium Dextran Sulfate. To drive phase separation in coincidence with gravity, the electric field is applied at an intensity of 5.1 volt per centimeter with the anode being disposed above the chamber and the cathode disposed beneath the chamber. It has been found in practice that separation rate increases as the intensity of the field is increased.

Since biological cells are known to exhibit characteristic electrophoretic mobilities, the possibilities should be considered that an electric field applied to drive phase separation can affect the cell partitioning process. Cell electrophoresis might, for example, pull cells out of the interface and thus change their position in the system.

Conversely, for most phase systems used in cell separation work, partition occurs between the top phase and the interface with no cells remaining in the bottom phase. When the electric field is applied, the cells which have partitioned into the top phase will tend to move closer to the top electrode. cells adsorbed at the interface will also tend to move in this direction, but the interfacial tension is sufficient to hold the cells in place. For the field strengths in the order hereinbefore mentioned, the cells tend to remain in the interface as the droplets are moved at velocities of one to two orders of magnitude greater than those at which the cells alone move in a free suspension. The latter velocities are very small compared to droplet velocities because of relatively high phase viscosity and a low cell potential. The interfacial tension is apparently strong enough to maintain the relative position of the cells in the interface in conditions similar to those present during field-driven phase separation.

Experimentally, it has been shown that a low-level, selectively-applied field, such as five volts per centimeter, can accelerate the separation of phases by a very large factor such as, for example, thirty-five-fold in a one G environment. An electric field can, therefore, be very effective in a celestial space environment, or in a gravity field of less than one G, for achieving phase separation.

Consequently, the use of an electric field constitutes a practical solution to the problem of implementing countercurrent distribution in space and permits the countercurrent distribution technique to be employed in separating large cell mixtures for which it has not heretofore been applicable, due to rapid settling effects. Moreover, it has been shown that electrophoretic migration of the individual cells will be of a negligible disturbing factor. The phase forming polymers heretofore described generally are not considered to be particularly compatible with biological cells. However, biocompatible phase forming polymers have been used successfully in achieving phase separation by the technique heretofore described.

In view of the foregoing, it is believed to be readily apparent that the method hereinbefore disclosed provides a practical solution to problems encountered in employing countercurrent distribution as a cell separating technique.

I claim:
1. In a method for separating biological cells, the steps comprising:
   A. depositing in a separation chamber a cell suspending medium consisting of an aqueous polymer system including at least one phase which exhibits electrophoretic mobility in an electrostatic field; and
   B. establishing between a pair of electrodes in an electrostatic field extending across the separation chamber for causing droplets of said phase to migrate toward one electrode of said pair.

2. In a method as defined in claim 1 wherein said droplets are characterized by a finite surface potential.

3. In a method for separating biological cells the steps comprising:
   A. depositing a mixed cell population in a suspending medium comprising an aqueous polymer system including at least one phase for which certain cells of the population exhibit an affinity and are characterized by electrophoretic mobility;
   B. depositing the medium in a phase separation chamber; and
   C. establishing an electrostatic field extending across the chamber of a magnitude sufficient to effect phase separation for said one phase with attendant cell separation for said certain cells.

4. In a method as defined in claim 3 wherein said separation chamber is disposed in a one G environment, said electrostaic field is applied vertically across the chamber, and said one phase is caused to migrate upwardly for transporting said certain cells toward the top of the chamber against the gravity field of the environment.

5. In a method as defined in claim 4 wherein droplets of said one phase are characterized by a negative surface potential.

6. In a method for separating biological cells, the steps comprising:
   A. suspending a mixed cell population in an aqueous polymer system consisting of phases for which said cells exhibit an affinity including at least one phase having droplets characterized by a negative surface potential and at least one phase having droplets characterized by a positive surface potential; and
   B. subjecting a body of said system to an electrostatic field established between a pair of electrodes and extended across the body, said field being of sufficient intensity for causing said droplets to migrate toward said electrodes with attendant separation of the cells of said population.

7. In a method for separating biological cells as defined in claim 6 wherein said body is subjected to a gravitational field of one G, said electrostatic field is established between an anode disposed above said body and a cathode disposed beneath said body, whereby control of directional migration is achieved over the droplets and cells exhibiting electrophoretic characteristics.

8. In a method for separating biological cells as defined in claim 6 wherein said body is subjected to a gravitational field of less than one G.

* * * * *